US006365217B2

(12) United States Patent
Fotos et al.

(10) Patent No.: US 6,365,217 B2
(45) Date of Patent: Apr. 2, 2002

(54) N-[N-(3,3-DIMETHYLBUTYL)-L-α-ASPARTYL]-L-PHENYLALANINE 1-METHYL ESTER AGGLOMERATE

(75) Inventors: Jim Fotos, Wheeling; Ihab Bishay, Mundelein, both of IL (US)

(73) Assignee: The Nutra Sweet Company, Chicago, IL (US)

( * ) Notice: Subject to any disclaimer, the term of this patent is extended or adjusted under 35 U.S.C. 154(b) by 0 days.

(21) Appl. No.: 09/727,487

(22) Filed: Dec. 4, 2000

Related U.S. Application Data

(62) Division of application No. 09/252,072, filed on Feb. 18, 1999, now Pat. No. 6,180,157.

(51) Int. Cl.$^7$ ............................................. A23L 1/236
(52) U.S. Cl. ........................ 426/548; 426/89; 426/96; 560/40
(58) Field of Search ............................ 426/548, 89, 96, 426/103; 560/40, 41

(56) References Cited

U.S. PATENT DOCUMENTS

| | | | |
|---|---|---|---|
| 2,856,290 A | 10/1958 | Peebles | 99/139 |
| 3,251,695 A | 5/1966 | Gidlow et al. | 99/94 |
| 3,433,644 A | 3/1969 | Ganske et al. | 99/78 |
| 3,615,670 A | 10/1971 | Sienkiewicz et al. | 99/71 |
| 3,761,288 A | 9/1973 | Glicksman et al. | 99/141 A |
| 3,868,472 A | 2/1975 | Berg et al. | 426/342 |
| 3,923,369 A | 12/1975 | Glicksman et al. | 426/548 |
| 3,928,633 A | 12/1975 | Shoat et al. | 426/96 |
| 4,001,456 A | 1/1977 | Glicksman et al. | 426/548 |
| 4,554,167 A | 11/1985 | Sorge et al. | 426/285 |
| 5,480,668 A | 1/1996 | Nofre et al. | 426/548 |
| 5,510,508 A | 4/1996 | Claude et al. | 560/41 |
| 5,728,862 A | 3/1998 | Prakash | 560/40 |

FOREIGN PATENT DOCUMENTS

| | | |
|---|---|---|
| WO | 98/39979 | 9/1998 |
| WO | 99/62354 | 12/1999 |

*Primary Examiner*—Leslie Wong
(74) *Attorney, Agent, or Firm*—Fitzpatrick, Cella, Harper & Scinto; Jeffrey M Hoster

(57) ABSTRACT

This invention provides a process for preparing an agglomerate of N-[N-(3,3-dimethylbutyl)-L-α-aspartyl]-L-phenylalanine 1-methyl ester and a carrier including the steps of: (a) providing a premix solution containing N-[N-(3,3-dimethylbutyl)-L-α-aspartyl]-L-phenylalanine 1-methyl ester and a binding agent; (b) fluidizing a carrier; and (c) applying the premix solution of step (a) onto said fluidized carrier to form an agglomerate of said N-[N-(3,3-dimethylbutyl)-L-α-aspartyl]-L-phenylalanine 1-methyl ester and said carrier. This invention is also directed to the novel agglomerates prepared by the process of this invention.

111 Claims, No Drawings

N-[N-(3,3-DIMETHYLBUTYL)-L-α-ASPARTYL]-L-PHENYLALANINE 1-METHYL ESTER AGGLOMERATE

This application is a divisional of Ser. No. 09/252,072, filed Feb. 18, 1999, now U.S. Pat. No. 6,180,157.

BACKGROUND OF THE INVENTION

1. Field of the Invention

The present invention relates to a process for preparing agglomerates of N-[N-(3, 3-dimethylbutyl)-L-α-aspartyl]-L-phenylalanine 1-methyl ester (also known as neotame) and a carrier. The invention also relates to the novel agglomerates.

2. Discussion of the Related Art

N-[N-(3,3-dimethylbutyl)-L-α-aspartyl]-L-phenylalanine 1-methyl ester is a derivative of aspartame that has a sweetening potency that is about 40 to 50 times that of aspartame (and about 8,000 times that of sucrose). N-[N-(3,3-dimethylbutyl)-L-α-aspartyl]-L-phenylalanine 1-methyl ester may be prepared from aspartame as described in U.S. Pat. Nos. 5,480,668, 5,510,508, and 5,728,862, all of which are incorporated by reference herein.

Structurally, N-[N-(3,3-dimethylbutyl)-L-α-aspartyl]-L-phenylalanine 1-methyl ester and aspartame differ in that, in N-[N-(3,3-dimethylbutyl)-L-α-aspartyl]-L-phenylalanine 1-methyl ester, a bulky neohexyl substituent is present on the amine nitrogen.

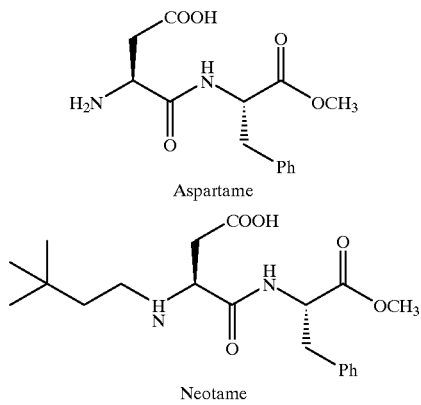

Aspartame

Neotame

This structural difference results in dramatic differences in the physical and chemical properties of these compounds. For example, the melting point of N-[N-(3,3-dimethylbutyl)-L-α-aspartyl]-L-phenylalanine 1-methyl ester is about 82.2° C., while that of aspartame is 248° C. In addition, N-[N-(3,3-dimethylbutyl)-L-α-aspartyl]-L-phenylalanine 1-methyl ester has much higher solubility in organic solvents than aspartame. It is also known that N-[N-(3,3-dimethylbutyl)-L-α-aspartyl]-L-phenylalanine 1-methyl ester has a higher stability than aspartame under some pH conditions, as described in U.S. Pat. No. 5,480,688. The pronounced difference in sweetness between the two compounds is further evidence of their chemical dissimilarity.

The solubility of N-[N-(3,3-dimethylbutyl)-L-α-aspartyl]-L-phenylalanine 1-methyl ester in water is about 1%, which is approximately equal to the water solubility of other high intensity sweeteners such as aspartame. However, while the solubility of other high intensity sweeteners in ethanol is very low (e.g., less than 0.1% for aspartame), the solubility of N-[N-(3,3-dimethylbutyl)-L-α-aspartyl]-L-phenylalanine 1-methyl ester in ethanol is greater than 100 g/100 ml.

Thus, unlike less soluble sweeteners such as aspartame which are agglomerated as a powder onto a powder carrier, N-[N-(3,3-dimethylbutyl)-L-α-aspartyl]-L-phenylalanine 1-methyl ester may be agglomerated as a solution onto a powder carrier. The process of agglomeration using a N-[N-(3,3-dimethylbutyl)-L-α-aspartyl]-L-phenylalanine 1-methyl ester solution, rather than a powder, provides numerous significant advantages including improved content uniformity and ease of processing.

N-[N-(3,3-dimethylbutyl)-L-α-aspartyl]-L-phenylalanine 1-methyl ester may be used for sweetening a variety of products, including drinks, foods, confectionery, pastries, chewing gums, hygiene products and toiletries, as well as cosmetic, pharmaceutical and veterinary products. Its superior sweetening potency makes N-[N-(3,3-dimethylbutyl)-L-α-aspartyl]-L-phenylalanine 1-methyl ester an attractive alternative to aspartame because it permits the use of N-[N-(3,3-dimethylbutyl)-L-α-aspartyl]-L-phenylalanine 1-methyl ester in substantially smaller quantities than is required for aspartame to achieve an equivalent sweetening effect.

Because of N-[N-(3,3-dimethylbutyl)-L-α-aspartyl]-L-phenylalanine 1-methyl ester's superior potency, it is convenient to prepare compositions of N-[N-3,3-dimethylbutyl)-L-α-aspartyl]-L-phenylalanine 1-methyl ester which deliver sweetness on par with that of aspartame. For liquid products such as beverages, this may be accomplished by preparing dilute solutions of N-[N-(3,3-dimethylbutyl)-L-α-aspartyl]-L-phenylalanine 1-methyl ester. Since N-[N-(3,3-dimethylbutyl)-L-α-aspartyl]-L-phenylalanine 1-methyl ester's sweetening potency is about 40 times greater than that of aspartame, these solutions can be prepared using about 2.5% as much N-[N-(3,3-dimethylbutyl)-L-α-aspartyl]-L-phenylalanine 1-methyl ester as would be required to prepare solutions of equal sweetness using aspartame. This amount can be adjusted to take into account the relative potency differences relating to the concentration effect of the respective sweeteners.

For solid products, such as tabletop sugar substitutes, this may be accomplished by forming a dry blend of N-[N-(3, 3-dimethylbutyl)-L-α-aspartyl]-L-phenylalanine 1-methyl ester with a bulking agent such as, for example, Unidex brand mixture of dextrose (97%) and maltodextrin (3%) available from CPC International. It is common to blend 95% by weight Unidex with 5% by weight aspartame to provide a tabletop sugar substitute. An equivalent N-[N-(3, 3-dimethylbutyl)-L-α-aspartyl]-L-phenylalanine 1-methyl ester sugar substitute would require blending about 99.875% by weight Unidex with about 0.125% by weight N-[N-(3, 3-dimethylbutyl)-L-α-aspartyl]-L-phenylalanine 1-methyl ester.

The use of small amounts of N-[N-(3,3-dimethylbutyl)-L-α-aspartyl]-L-phenylalanine 1-methyl ester powder to prepare dry blends with a bulking agent presents several manufacturing difficulties. Not surprisingly, dry blends prepared using a relatively small amount of N-[N-(3,3-dimethylbutyl)-L-α-aspartyl]-L-phenylalanine 1-methyl ester and a relatively large amount of a bulking agent may exhibit poor content uniformity. Because of the relatively small amount of N-[N-(3,3-dimethylbutyl)-L-α-aspartyl]-L-phenylalanine 1-methyl ester as compared to bulking agent, these dry blends also may exhibit a high degree of segregation and dusting. Moreover, the content uniformity and segregation problems associated with such dry blends often worsen during shipping and also during periods of storage. Consequently, these dry blends may be somewhat unattractive for manufacturers of consumer products as well as for consumers.

It would be highly desirable to overcome the difficulties described above by preparing agglomerates of N-[N-(3,3-dimethylbutyl)-L-α-aspartyl]-L-phenylalanine 1-methyl ester with a carrier and using the agglomerates to provide N-[N-(3,3-dimethylbutyl)-L-α-aspartyl]-L-phenylalanine 1-methyl ester in a deliverable form. In addition, it would be extremely advantageous to provide a tabletop sweetener with agglomerates of N-[N-(3,3-dimethylbutyl)-L-α-aspartyl]-L-phenylalanine 1-methyl ester. Similarly, it would be extremely advantageous to provide a powdered soft drink mix with agglomerates of N-[N-(3,3-dimethylbutyl)-L-α-aspartyl]-L-phenylalanine 1-methyl ester. It is also important to deliver a blend of sweetness in an efficient manner.

Fluidized bed agglomeration is well known in the art. The process is described in U.S. Pat. Nos. 2,856,290, 3,251,695, and 3,433,644, the disclosures of which are incorporated by reference herein. Typically, in both continuous and batch fluid bed agglomeration processes, finely divided particles are sprayed onto a fluidized bed of particles under moisture and temperature conditions which promote formation of an agglomerate. Often the process involves heating at least one of the components of the agglomerate to a temperature above its melting point.

U.S. Pat. No. 4,554,167 discloses a method for preparing agglomerates of aspartame and acid-containing food mixes. The disclosed agglomeration process does not involve heating one or more of the agglomerate components to a temperature above its melting point. Neither does the disclosed proceed involve dissolving the high intensity sweetener in a solvent prior to formation of the agglomerate.

Agglomerates of N-[N-(3,3-dimethylbutyl)-L-α-aspartyl]-L-phenylalanine 1-methyl ester would facilitate adjustment of the amount of N-[N-(3,3-dimethylbutyl)-L-α-aspartyl]-L-phenylalanine 1-methyl ester to be delivered. These agglomerates also would provide N-[N-(3,3-dimethylbutyl)-L-α-aspartyl)-L-phenylalanine 1-methyl ester preparations with excellent content uniformity. In addition, these agglomerates also would exhibit reduced segregation and dusting as compared to the N-[N-(3,3-dimethylbutyl)-L-α-aspartyl]-L-phenylalanine 1-methyl ester dry blend preparations.

SUMMARY OF THE INVENTION

This invention provides a process for preparing an agglomerate of N-[N-(3,3-dimethylbutyl)-L-α-aspartyl]-L-phenylalanine 1-methyl ester and a carrier comprising the steps of: (a) providing a premix solution comprising N-[N-(3,3-dimethylbutyl)-L-α-aspartyl]-L-phenylalanine 1-methyl ester and a binding agent; (b) fluidizing a carrier; and (c) applying the premix solution of step (a) onto said fluidized carrier to form an agglomerate of said N-[N-(3,3-dimethylbutyl)-L-α-aspartyl]-L-phenylalanine 1-methyl ester and said carrier. This invention is also directed to the novel agglomerates prepared by the process of this invention. This invention is also directed to tabletop sweeteners, powdered soft drink mixes and sweetener blends having the above-described agglomerates.

DETAILED DESCRIPTION OF THE INVENTION

In the agglomeration process of the present invention, a premix solution is formed which comprises N-[N-(3,3-dimethylbutyl)-L-α-aspartyl]-L-phenylalanine 1-methyl ester and a binding agent. The premix solution may be formed by adding the N-[N-(3,3-dimethylbutyl)-L-α-aspartyl]-L-phenylalanine 1-methyl ester and the binding agent to the same solvent. Alternatively, the premix solution may be formed by adding the N-[N-(3,3-dimethylbutyl)-L-α-aspartyl]-L-phenylalanine 1-methyl ester and the binding agent to separate solvents and then combining the two solutions. In the latter approach, the solvent used to dissolve the N-[N-(3,3-dimethylbutyl)-L-α-aspartyl]-L-phenylalanine 1-methyl ester may be the same as, or different from, the solvent used to dissolve the binding agent. Under either process, the resultant premix is applied onto a fluidized carrier using a fluid bed agglomeration mixer. Preferably, the premix is applied onto the fluidized carrier by spraying the premix onto the fluidized carrier. An agglomerate of N-[N-(3,3-dimethylbutyl)-L-α-aspartyl]-L-phenylalanine 1-methyl ester and the carrier is thus formed.

The agglomerates of this invention comprise: (i) an effective sweetener amount of N-[N-(3,3-dimethylbutyl)-L-α-aspartyl]-L-phenylalanine 1-methyl ester; (ii) a binding agent; and (iii) a carrier. The binders and carriers employed in the agglomerates of this invention are described in greater detail herein.

The agglomeration process of the present invention may be performed using a batch fluid bed agglomerator. Other equipment that may be used in the present invention include a continuous fluid bed agglomerator or a continuous turbulent flow agglomerator (e.g., Schugi Flex-O-Mix and Turbulizer, Hosokawa Bepex Corp., Minneapolis, Minn.).

In order to prepare the premix solution, N-[N-(3,3-dimethylbutyl)-L-α-aspartyl]-L-phenylalanine 1-methyl ester is added to a solvent. Any solvent in which N-[N-(3,3-dimethylbutyl)-L-α-aspartyl]-L-phenylalanine 1-methyl ester dissolves may be used in the present invention. Preferably, the solvent is a food grade solvent. Exemplary solvents which may be used in this invention include ethanol, water, isopropanol, methanol, and mixtures thereof, Preferably, the solvent is ethanol.

The binding agent is dissolved in a solvent which may be the same as, or different from, the solvent used to dissolve the N-[N-(3,3-dimethylbutyl)-L-α-aspartyl]-L-phenylalanine 1-methyl ester. Any solvent in which the particular binding agent chosen dissolves may be used in the present invention. Solvents which may be used to dissolve the binding agent include water, ethanol, isopropanol, methanol and mixtures thereof. Preferably, the solvent is a food grade solvent. Most preferably, the solvent is water.

As mentioned above, it is not necessary to dissolve the N-[N-(3,3-dimethylbutyl)-L-α-aspartyl]-L-phenylalanine 1-methyl ester in one solvent, the binding agent in a separate solvent, and then combine the two solutions to form a premix. As is readily apparent to those skilled in the art, the premix solution may be prepared by dissolving the N-[N-(3,3-dimethylbutyl)-L-α-aspartyl]-L-phenylalanine 1-methyl ester and the binding agent in the same solvent, The solvent may be a single compound (e.g., ethanol), or it may be a mixture of compounds (e.g., ethanol and water). This invention is not limited in the manner of making the premix of the invention.

In order to effect complete mixing of the premix, the premix may be heated up to about 90° C. As used herein, the term "effect mixing" means blending sufficiently so as to form a mixture. Preferably, the premix solution is heated to between about 30° C. and about 50° C., more preferably between about 35° C. and about 45° C.

The carrier is fluidized and its temperature is adjusted to between about 20° C. and about 50° C. Preferably, the carrier is heated to between about 35° C. and about 45° C. More preferably, the carrier is heated to about 40° C.

The carrier may be placed into a removable bowl of a fluid bed agglomerator. After the bowl is secured to the fluid bed agglomerator, the carrier is fluidized and heated as necessary by adjusting the inlet air temperature. Preferably, the temperature of the inlet air is maintained between 50° C. and 100° C. For example, to heat the fluidized carrier to about 40° C., the inlet air temperature may be adjusted to between 70° C.–75° C.

Once the fluidized carrier reaches the desired temperature, the premix solution may be applied through the spray nozzle of the fluid bed agglomerator. The premix solution may be sprayed onto the fluidized carrier at any rate which is effective to produce an agglomerate having the desired particle size distribution. Those skilled in the art will recognize that a number of parameters may be adjusted to obtain the desired particle size distribution. After spraying is completed, the agglomerate may be allowed to dry. Preferably, the agglomerate is allowed to dry until the outlet air temperature reaches 35° C. to 40° C.

As stated above, the solubility of N-[N-(3,3-dimethylbutyl)-L-α-aspartyl]-L-phenylalanine 1-methyl ester in ethanol is greater than 100 g/100 ml. In contrast, the solubility of other high intensity sweeteners in ethanol is very low (e.g., less than 0.1% for aspartame).

As a result of N-[N-(3,3-dimethylbutyl)-L-α-aspartyl]-L-phenylalanine 1-methyl ester's unusually high solubility in ethanol and other alcohols, solutions of N-[N-(3,3-dimethylbutyl)-L-α-aspartyl]-L-phenylalanine 1-methyl ester in ethanol may be prepared over a broad range of concentrations. Such solutions may be used in a fluidized bed agglomeration process to make N-[N-(3,3-dimethylbutyl)-L-α-aspartyl]-L-phenylalanine 1-methyl ester agglomerates with various carriers. The resultant N-[N-(3,3-dimethylbutyl)-L-α-aspartyl]-L-phenylalanine 1-methyl ester agglomerates provide a delivery vehicle for N-[N-(3,3-dimethylbutyl)-L-α-aspartyl]-L-phenylalanine 1-methyl ester in a form which is convenient for use in many food applications.

As a result of the very small amount of N-[N-(3,3-dimethylbutyl)-L-α-aspartyl]-L-phenylalanine 1-methyl ester used, the amount of ethanol required for solubilization is insignificant. In contrast, even if other high intensity sweeteners could be solubilized in ethanol, the amount of ethanol required could be cause for concern.

An advantageous feature of the present invention is that the level of N-[N-(3,3-dimethylbutyl)-L-α-aspartyl]-L-phenylalanine 1-methyl ester that is present in these agglomerates may be controlled by varying the amount of N-[N-(3,3-dimethylbutyl)-L-α-aspartyl]-L-phenylalanine 1-methyl ester that is added to the premix solution. This is particularly important when trying to match the sweetness delivered by other sweeteners such as aspartame in different products at different concentration levels. The use of a N-[N-(3,3-dimethylbutyl)-L-α-aspartyl]-L-phenylalanine 1-methyl ester/binding agent premix also provides advantages in the manufacturing process by facilitating the preparation of especially desirable tabletop products.

Another advantageous aspect of the present invention is that the N-[N-(3,3-dimethylbutyl)-L-α-aspartyl]-L-phenylalanine 1-methyl ester agglomerates may be blended with blending agents. As used herein, the term blending agents includes a broad range of ingredients commonly used in foods or beverages including, but not limited to, those used herein as binding agents, carriers, bulking agents, and sweeteners. Exemplary blending agents that may be blended with the N-[N-(3,3-dimethylbutyl)-L-α-aspartyl]-L-phenylalanine 1-methyl ester agglomerates of this invention include aspartame, acesulfame and its salts, sucralose, saccharin, alitame, cyclamates, stevia derivatives, thaumatin, sucrose, fructose, dextrose, polyol sugar alcohols, citric acid, dextrin, maltodextrin, dextrose-maltodextrin blends, lactose, inulin, erythritol, sorbitol, stevioside, hydroxypropylmethyl cellulose, carboxymethyl cellulose, polyvinylpyrrolidone, and mixtures thereof. A preferred blending agent that may be dry blended with the N-[N-(3,3-dimethylbutyl)-L-α-aspartyl]-L-phenylalanine 1-methyl ester agglomerates of this invention is Unidex.

Such blends are particularly convenient to manufacture, as they take advantage of procedures used in conventional tabletop manufacturing processes. To illustrate, in conventional manufacturing of tabletop sweeteners with aspartame, the aspartame alone is blended with Unidex. The agglomerate of this invention can be tailored to match the level of sweetness and bulk of aspartame, thereby allowing the agglomerate to be a 1:1 substitute for aspartame. Thus, the agglomerates of this invention provide great flexibility in the use of N-[N-(3,3-dimethylbutyl)-L-α-aspartyl]-L-phenylalanine 1-methyl aster in consumer products which use high intensity sweeteners.

The N-[N-(3,3-dimethylbutyl)-L-α-aspartyl]-L-phenylalanine 1-methyl ester agglomerates of this invention may be dry blended with blending agents to prepare highly desirable consumer products. For example, the agglomerates of this invention may be used to prepare particularly desirable tabletop sweeteners and powdered soft drink mixes. The tabletop sweeteners and powdered soft drink mixes of this invention may be prepared by dry blending the agglomerates of this invention with blending agents commonly used to prepare tabletop sweeteners and powdered soft drink mixes using methods well known to those skilled in the art.

The N-[N-(3,3-dimethylbutyl)-L-α-aspartyl]-L-phenylalanine 1-methyl ester agglomerates of this invention may be dry blended with sweeteners to provide highly desirable sweetener blends. Exemplary sweeteners that may be dry blended with the N-[N-(3,3-dimethylbutyl)-L-α-aspartyl]-L-phenylalanine 1-methyl ester agglomerates of this invention include aspartame, acesulfame and its salts, sucralose, saccharin, alitame, cyclamates, stevia derivatives, thaumatin, sucrose, fructose, dextrose, polyol sugar alcohols, and mixtures thereof. It is also possible to prepare agglomerates containing N-[N-(3,3-dimethylbutyl)-L-α-aspartyl]-L-phenylalanine 1-methyl ester and one of the above described other sweeteners.

The amount of N-[N-(3,3-dimethylbutyl)-L-α-aspartyl]-L-phenylalanine 1-methyl ester agglomerate that may be present in the sweetener blends of this invention may vary over a broad range. The agglomerate of this invention are extremely compatible for blending with other sweeteners in a wide range of usage levels. This compatibility will allow one skilled in the art to readily formulate the blends depending upon the desired end use functionality.

Another advantageous feature of the present invention is that the concentration of N-[N-(3,3-dimethylbutyl)-L-α-aspartyl]-L-phenylalanine 1-methyl ester in the solvent may vary widely depending upon the particular solvent used, as well as upon the desired level of N-[N-(3,3-dimethylbutyl)-L-α-aspartyl]-L-phenylalanine 1-methyl ester in the agglomerate. Thus, where it is desired to have a high level of N-[N-(3,3-dimethylbutyl)-L-α-aspartyl]-L-phenylalanine 1-methyl ester in the agglomerate, a greater amount of N-[N-(3,3-dimethylbutyl)-L-α-aspartyl]-L-phenylalanine 1-methyl ester would be dissolved in the solvent. Conversely, where it is desired to have a low level of N-[N-(3,3-dimethylbutyl)-L-α-aspartyl]-L-phenylalanine 1-methyl ester in the agglomerate, a lesser amount of N-[N-(3,3-dimethylbutyl)-L-α-aspartyl]-L-phenylalanine 1-methyl ester may be dissolved in the solvent.

The available range of concentration of N-[N-(3,3-dimethylbutyl)-L-α-aspartyl]-L-phenylalanine 1-methyl ester in the solvent will, of course, depend upon the solubility of N-[N-(3,3-dimethylbutyl)-L-α-aspartyl]-L-phenylalanine 1-methyl ester in the particular solvent chosen.

A particular advantage of the present invention is that because of N-[N-(3,3-dimethylbutyl)-L-α-aspartyl]-L-phenylalanine 1-methyl ester's solubility properties in ethanol, the broad range of concentrations that can be achieved may be used to produce a broad range of concentrations of N-[N-(3,3-dimethylbutyl)-L-α-aspartyl]-L-phenylalanine 1-methyl ester in the agglomerate.

A large number of solvents may be used in the process of this invention, depending upon the particular processing conditions employed. When ethanol is used as the solvent, the available range of concentrations of N-[N-(3,3-dimethylbutyl)-L-α-aspartyl]-L-phenylalanine 1-methyl ester is very broad. For example, the concentration of N-[N-(3,3-dimethylbutyl)-L-α-aspartyl]-L-phenylalanine 1-methyl ester in ethanol solutions may be between about 0.01% and about 50% by weight. Preferably, the concentration of N-[N-(3,3-dimethylbutyl)-L-α-aspartyl]-L-phenylalanine 1-methyl ester in ethanol solutions will be between about 1% and about 15%, more preferably between about 5% and about 10% by weight.

Binding agents facilitate the agglomeration of N-[N-(3,3-dimethylbutyl)-L-α-aspartyl]-L-phenylalanine 1-methyl ester to the carrier. Any binding agent with sufficient binding strength may be used in the present invention. Exemplary binding agents which may be used in the present invention include maltodextrin, sucrose, gellan gum, hydroxypropylmethyl cellulose (HPMC), carboxymethyl cellulose (CMC), polyvinyl pyrrolidone (PVP) and mixtures thereof. Preferably, the binding agent is maltodextrin.

The concentration of binding agent in the solution may vary depending on a variety of factors including the binding strength of the particular binding agent and the particular solvent chosen. When water is the solvent, it is preferable that the concentration of binding agent in the aqueous solution be between about 1% and about 50% by weight. More preferably, the concentration of binding agent in the aqueous solution is between about 5% and about 25% by weight.

The weight ratio of binding agent to N-[N-(3,3-dimethylbutyl)-L-α-aspartyl]-L-phenylalanine 1-methyl ester in the premix solution may vary from as low as about 1:10 to as high as about 10:1. Preferably, the weight ratio of binding agent to N-[N-(3,3-dimethylbutyl)-L-α-aspartyl]-L-phenylalanine 1-methyl ester is from about 0.5:1.0 to about 2:1.

An advantageous aspect of this invention is that the premixes of this invention provide excellent formulation flexibility. These premixes enable the agglomerates of this invention to be used as delivery vehicles for,other ingredients, such as, for example, flavors. Consequently, the agglomerates of this invention may be used as flavor modifiers. The use of N-[N-(3,3-dimethylbutyl)-L-α-aspartyl]-L-phenylalanine 1-methyl ester as a flavor modifier is discussed in U.S. Provisional Patent Application No. 60/112,948, filed on Dec. 18, 1998, the entire contents of which are incorporated by reference herein.

The premixes of this invention may be used in the process of the present invention to provide an agglomerate comprising (i) an effective sweetener amount of N- [N- (3 , 3-dimethylbutyl)-L-α-aspartyl]-L-phenylalanine 1-methyl ester; (ii) a binding agent; (iii) a carrier; and (iv) an adjuvant, for example, a sweetener, a flavor or the like. Such an agglomerate may be prepared by adding the sweetener or other soluble adjuvant to the premix before the premix is applied to the carrier. Any soluble adjuvant which enhances the temporal properties of the agglomerate may be used in this invention. Adjuvants which may be added to the premix include, for example, glycerin and flavors.

The carriers which may be used in the present invention include, for example, dextrose, citric acid, maltodextrin, dextrose-maltodextrin blends, lactose, inulin, erythritol, sorbitol, sucrose, aspartame, acesulfame and its salts, sucralose, cyclamate, saccharin, stevioside, alitame and mixtures thereof.

The weight ratio of carrier to N-[N-(3,3-dimethylbutyl)-L-α-aspartyl]-L-phenylalanine 1-methyl ester may vary considerably depending upon a number of factors including the selection of binding agent and carrier, as well as the desired sweetening potency of the agglomerate. Generally, the weight ratio of carrier to N-[N-(3,3-dimethylbutyl)-L-α-aspartyl]-L-phenylalanine 1-methyl ester will be between 200:1 and 5:1. Preferably, the weight ratio should be between 100:1 and 40:1.

The amount of N-[N-(3,3-dimethylbutyl)-L-α-aspartyl]-L-phenylalanine 1-methyl ester present in the agglomerates of the present invention may vary over a broad range, depending upon the particular end use desired. Preferably, the amount of N-[N-(3,3-dimethylbutyl)-L-α-aspartyl]-L-phenylalanine 1-methyl ester present in the agglomerates of the present invention is between about 0.001 weight percent and about 50 weight percent based upon the total amount of the agglomerate. More preferably, the amount of N-[N-(3,3-dimethylbutyl)-L-α-aspartyl]-L-phenylalanine 1-methyl ester is between about 0.1 weight percent and about 5 weight percent.

The amount of carrier present in the agglomerates of the present invention also may vary over a broad range, depending upon the particular carrier selected as well as the end use desired. Preferably, the amount of carrier present in the agglomerates of the present invention is between about 50 weight percent and about 99.9 weight percent based upon the total amount of the agglomerate. More preferably, the amount of carrier is between about 75 weight percent and about 99 weight percent.

The amount of binding agent present in the agglomerates of the present invention also may vary over a broad range, depending upon the particular binding agent selected as well as the end use desired. Preferably, the amount of binding agent present in the agglomerates of the present invention is between about 0.1 weight percent and about 15 weight percent based upon the total amount of the agglomerate. More preferably, the amount of binding agent is between about 1 weight percent and about 7 weight percent.

The agglomerates of this invention may be dry blended with blending agents to prepare various products including, for example, tabletop sweeteners and powdered soft drink mixes. Exemplary blending agents which may be dry blended with the agglomerates of this invention include aspartame, acesulfame and its salts, sucralose, saccharin, alitame, cyclamates, stevia derivatives, thaumatin, sucrose, fructose, dextrose, polyol sugar alcohols, citric acid, dextrin, maltodextrin, dextrose-maltodextrin blends, lactose, inulin, erythritol, sorbitol, stevioside, hydroxypropylmethyl cellulose, carboxymethyl cellulose, polyvinylpyrrolidone, and mixtures thereof.

The amount of N-[N-(3,3-dimethylbutyl)-L-α-aspartyl]-L-phenylalanine 1-methyl ester agglomerate that may be present in the tabletop sweeteners of this invention may vary over a broad range. Preferably, the amount of N-[N-(3,3-dimethylbutyl)-L-α-aspartyl]-L-phenylalanine 1-methyl ester agglomerate present in the tabletop sweeteners of this invention is between about 0.01 weight percent and about 100 weight percent based upon the total amount of the tabletop sweetener. More preferably, the amount of N-[N-(3,3-dimethylbutyl)-L-α-aspartyl]-L-phenylalanine 1-methyl ester agglomerate is between about 0.5 weight percent and about 30 weight percent. Most preferably, the amount of N-[N-(3,3-dimethylbutyl)-L-α-aspartyl]-L-phenylalanine 1-methyl ester agglomerate is between about 1 weight percent and about 10 weight percent.

The amount of blending agent that may be present in the tabletop sweeteners of this invention may vary over a broad range. Preferably, the amount of blending agent present in the tabletop sweeteners of this invention is between about 50 weight percent and about 99 weight percent based upon the total amount of the tabletop sweetener. More preferably, the amount of blending agent is between about 90 weight percent and about 99 weight percent.

The amount of N-[N-(3,3-dimethylbutyl)-L-α-aspartyl]-L-phenylalanine 1-methyl ester agglomerate that may be present in the powdered soft drink mixes of this invention may vary over a broad range. Preferably, the amount of N-[N-(3,3-dimethylbutyl)-L-α-aspartyl]-L-phenylalanine 1-methyl ester agglomerate present in the powdered soft drink mixes of this invention is between about 4 weight percent and about 100 weight percent based upon the total amount of the powdered soft drink mix. More preferably, the amount of N-[N-(3,3-dimethylbutyl)-L-α-aspartyl]-L-phenylalanine 1-methyl ester agglomerate is between about 30 weight percent and about 45 weight percent. In particular, preblend products which carry flavors and then are dry blended are preferred. Such preblend products include, for example, citric acid or other dissolving aids.

The particle size distribution of the N-[N-(3,3-dimethylbutyl)-L-α-aspartyl]-L-phenylalanine 1-methyl ester agglomerate may be determined by sifting the agglomerate through screens of various sizes. For example, the agglomerate may be sifted with screens ranging in size from 14 mesh to 140 mesh or higher. Typically, at least about 65% of the particles of the agglomerate will pass through a 40 mesh screen and less than about 20% of the agglomerate particles will pass through 100 mesh screen. In general, less than about 70% of the particles of the agglomerate will pass through a 60 mesh screen and less than about 5% of the agglomerate particles will pass through a 140 mesh screen. Typically, at least 50% of the particles of the agglomerate are between about 60 mesh and 100 mesh in size.

The product may be screened to produce a narrower particle size distribution, if desired. For example, a 14 mesh screen may be used to remove large particles and produce a product of especially good appearance. Particles smaller than 120 mesh may be removed to obtain an agglomerate with improved flow properties. A narrower particle size distribution may be obtained if desired for particular applications.

The particle size distribution of the N-[N-(3,3-dimethylbutyl)-L-α-aspartyl]-L-phenylalanine 1-methyl ester agglomerate may be controlled by a variety of factors including the selection of binding agent, the concentration of the binding agent in solution, the spray rate of the spray solution, the atomization air pressure and the particular carrier used. Those skilled in the art will appreciate that a desired particle size distribution may be obtained by varying one or more of the aforementioned factors. For example, increasing the spray rate is known to increase the average particle size.

The examples which follow are intended to illustrate certain preferred embodiments of the invention, and no limitation of the invention is implied.

EXAMPLE 1

Preparation of N-[N-(3,3-dimethylbutyl)-L-α-aspartyl]-L-phenylalanine 1-methyl ester/Dextrose Agglomerate Maltodextrin Binder 529 grams of N-[N-(3,3-dimethylbutyl)-L-α-aspartyl]-L-phenylalanine 1-methyl ester was dissolved in 3.143 Kg of ethanol. In a separate container, 635 grams of maltodextrin was dissolved in 7.333 Kg of water. The two solutions were combined and heated to 40° C. 20.0 Kg of dextrose was charged into a removable bowl of a batch fluid bed agglomeration unit. The dextrose was fluidized and heated to 40° C. by adjusting the inlet air temperature of the agglomeration unit to between 70° C. and 75° C. The N-[N-(3,3-dimethylbutyl)-L-α-aspartyl]-L-phenylalanine 1-methyl ester/maltodextrin solution was sprayed onto the fluidized dextrose at a spray rate of 200 ml/min. The atomization air pressure was maintained at 2.5 bar. The particle size distribution of the resulting N-[N-(3,3-dimethylbutyl)-L-α-aspartyl]-L-phenylalanine 1-methyl ester/dextrose agglomerate is set forth in Table 1.

EXAMPLE 2

Preparation of N-[N-(3,3-dimethylbutyl)-L-α-aspartyl]-L-phenylalanine 1-methyl ester/Dextrose Agglomerate Maltodextrin Binder A N-[N-(3,3-dimethylbutyl)-L-α-aspartyl]-L-phenylalanine 1-methyl ester/dextrose agglomerate was prepared as described in Example 1, except that the atomization air pressure was lowered to 1.5 bar. The particle size distribution of the resultant agglomerate is set forth in Table 1.

EXAMPLE 3

Preparation of N-[N-(3,3-dimethylbutyl)-L-α-aspartyl]-L-phenylalanine 1-methyl ester/Dextrose Agglomerate Maltodextrin Binder A N-[N-(3,3-dimethylbutyl)-L-α-aspartyl]-L-phenylalanine 1-methyl ester/dextrose agglomerate was prepared as described in Example 1, except that the atomization air pressure was lowered to 1.0 bar, and the spray rate was increased to 250–275 ml/min. The particle size distribution of the resultant agglomerate is set forth in Table 1.

EXAMPLE 4

Preparation of N-[N-(3,3-dimethylbutyl)-L-α-aspartyl]-L-phenylalanine 1-methyl ester/Dextrose Agglomerate

Hydroxypropylmethyl Cellulose Binder 539 grams of N-[N-(3,3-dimethylbutyl)-L-α-aspartyl]-L-phenylalanine 1-methyl ester was dissolved in 3.754 Kg of ethanol. In a separate container, 204 grams of hydroxypropylmethyl cellulose (HPMC) was dissolved in 8.759 Kg of water. The two solutions were combined to form a spray solution, and heated to 40° C. 20.0 Kg of dextrose was charged into a removable bowl of a batch fluid bed agglomeration unit. The dextrose was fluidized and heated to 38° C. to 40° C. The spray solution was applied to the fluidized dextrose using the spray nozzle of the agglomeration unit. The atomization air pressure was set at 1.5 bar. The particle size distribution of the resultant N-[N-(3,3-dimethylbutyl)-L-α-aspartyl]-L-phenylalanine 1-methyl ester/dextrose agglomerate is set forth in Table 1.

TABLE 1

Particle Size Distribution of N-[N-(3,3-dimethylbutyl)-L-α-aspartyl]-L-phenylalanine 1-methyl ester/Dextrose Agglomerates

| Screen Size | Ex. 1 | Ex. 2 | Ex. 3 | Ex. 4 |
|---|---|---|---|---|
| 20 Mesh | 0.00 | 0.10 | 0.50 | 0.10 |
| 40 Mesh | 2.70 | 3.80 | 5.50 | 9.00 |
| 60 Mesh | 21.90 | 35.40 | 38.50 | 69.80 |
| 100 Mesh | 82.10 | 90.10 | 89.80 | 97.40 |
| 140 Mesh | 94.30 | 98.90 | 99.10 | 99.90 |
| Pan | 4.70 | 1.10 | 0.90 | 0.10 |

EXAMPLE 5

Preparation of N-[N-(3,3-dimethylbutyl)-L-α-aspartyl]-L-phenylalanine 1-methyl ester/Citric Acid Agglomerate

Hydroxypropylmethyl Cellulose Binder 212 grams of N-[N-(3,3-dimethylbutyl)-L-α-aspartyl]-L-phenylalanine 1-methyl ester was dissolved in 900 grams of ethanol. In a separate container, 71 grams of HPMC was dissolved in 5.102 Kg of water. The two solutions were combined to form a spray solution, and heated to 40° C. 28.0 Kg of fine granular citric acid was charged into a removable bowl of a batch fluid bed agglomeration unit. The citric acid was fluidized and heated to 40° C. The spray solution was applied to the fluidized citric acid using the spray nozzle of the agglomeration unit. The atomization air pressure was maintained at 2.5 bar. The spray rate was set at 100 ml/min. The particle size distribution Of the resultant N-[N-(3,3-dimethylbutyl)-L-α-aspartyl]-L-phenylalanine 1-methyl ester/citric acid agglomerate is set forth in Table 2.

EXAMPLE 6

Preparation of N-[N-(3,3-dimethylbutyl)-L-α-aspartyl]-L-phenylalanine 1-methyl ester/Citric Acid Agglomerate

Hydroxypropylmethyl Cellulose Binder

A N-[N-(3,3-dimethylbutyl)-L-α-aspartyl]-L-phenylalanine 1-methyl ester/citric acid agglomerate was prepared as described in Example 5, except that the spray rate was increased to 150 ml/min. The particle size distribution of the resultant N-[N-(3,3-dimethylbutyl)-L-α-aspartyl]-L-phenylalanine 1-methyl ester/citric acid agglomerate is set forth in Table 2.

TABLE 2

Particle Size Distribution of N-[N-(3,3-dimethylbutyl)-L-α-aspartyl]-L-phenylalanine 1-methyl ester/Citric Acid Agglomerates

| Screen Size | Ex. 5 | Ex. 6 |
|---|---|---|
| 20 Mesh | 0.00 | 0.10 |
| 40 Mesh | 20.30 | 37.60 |
| 60 Mesh | 89.40 | 96.00 |
| 100 Mesh | 100.00 | 100.40 |
| Pan | 0.00 | 0.10 |

EXAMPLE 7

Preparation of Tabletop Sweetener Product with a N-[N-(3,3-dimethylbutyl)-L-α-aspartyl]-L-phenylalanine 1-methyl ester Agglomerate A tabletop sweetener product was prepared by blending a N-[N-(3,3-dimethylbutyl)-L-α-aspartyl]-L-phenylalanine 1-methyl ester/dextrose agglomerate prepared as described in Example 3 with Unidex using a 4.6 ft$^3$ Littleford Lodige high shear mixer (Littleford Brothers, Inc., Cincinnati, Ohio).

Eight 40 Kg batches of the tabletop sweetener were prepared by blending in each batch, 1.306 Kg of the N-[N-(3,3-dimethylbutyl)-L-α-aspartyl]-L-phenylalanine 1-methyl ester/dextrose agglomerate with 38.7 Kg of Unidex. The amount of N-[N-(3,3-dimethylbutyl)-L-α-aspartyl]-L-phenylalanine 1-methyl ester in each batch was therefore 0.07956 weight percent based on the total weight of the tabletop sweetener product.

After thorough mixing, six samples were taken from each batch and analyzed for N-[N-(3,3-dimethylbutyl)-L-α-aspartyl]-L-phenylalanine 1-methyl ester content. The results of these measurements are set forth in Table 3. These results show the excellent content uniformity that may obtained in products prepared according to the present invention. The 48 samples had an average N-[N-(3,3-dimethylbutyl)-L-α-aspartyl]-L-phenylalanine 1-methyl ester content of 0.07713%, with a standard deviation of 0.00361, and a relative standard deviation of only 4.68%.

TABLE 3

N-[N-(3,3-dimethylbutyl)-L-α-aspartyl]-L-phenylalanine 1-methyl ester content of Tabletop Sweetener Products

| Sample | Batch 1 | Batch 2 | Batch 3 | Batch 4 | Batch 5 | Batch 6 | Batch 7 | Batch 8 |
|---|---|---|---|---|---|---|---|---|
| 1 | 0.08334 | 0.07638 | 0.08067 | 0.07794 | 0.07624 | 0.07938 | 0.07808 | 0.07492 |
| 2 | 0.07532 | 0.07602 | 0.07941 | 0.07603 | 0.07834 | 0.08165 | 0.07231 | 0.07241 |
| 3 | 0.07782 | 0.07576 | 0.07440 | 0.08125 | 0.07638 | 0.09162 | 0.07708 | 0.07946 |
| 4 | 0.07532 | 0.07415 | 0.07465 | 0.07426 | 0.07634 | 0.07558 | 0.07932 | 0.07495 |
| 5 | 0.07333 | 0.07701 | 0.07174 | 0.08110 | 0.07628 | 0.08141 | 0.07752 | 0.07308 |
| 6 | 0.08052 | 0.07904 | 0.07618 | 0.07607 | 0.08188 | 0.07610 | 0.07246 | 0.07167 |

Other variations and modifications of this invention will be obvious to those skilled in the art. This invention is not limited except as set forth in the claims.

What is claimed is:

1. The product obtained by the process comprising the steps of:
   (a) providing a premix solution comprising N-{N-(3,3-dimethylbutyl)-L-α-aspartyl}-L-phenylalanine 1-methyl ester and a binding agent;
   (b) heating the premix solution of step (a) to a temperature effective to effect mixing of said premix;
   (c) fluidizing a carrier; and
   (d) applying the premix solution of step (b) onto said fluidized carrier to form an agglomerate comprising said N-{N-(3,3-dimethylbutyl)-L-α-aspartyl}-L-phenylalanine 1-methyl ester on said carrier.

2. The product of claim 1, wherein in step (d), said premix solution is applied onto said fluidized carrier by spraying said premix solution onto said fluidized carrier.

3. The product of claim 1, wherein step (a) comprises the steps of:
   (i) preparing a solution of N-(3,3-dimethylbutyl)-L-α-aspartyl]-L-phenylalanine 1-methyl ester;
   (ii) preparing a solution of a binding agent; and
   (iii) combining the solution of step (i) with the solution of step (ii).

4. The product of claim 1, wherein said premix solution further comprises a sweetener selected from the group consisting of aspartame, acesulfame salts, sucralose, saccharin, alitame, cyclamates, stevia derivatives, thaumatin, sucrose, fructose, dextrose, polyol sugar alcohols, and mixtures thereof.

5. The product of claim 1, wherein preparation of the premix solution comprises combining said N-[N-(3,3-dimethylbutyl)-L-α-aspartyl]-L-phenylalanine 1-methyl ester with a solvent selected from the group consisting of ethanol, isopropanol, methanol, water and mixtures thereof.

6. The product of claim 5, wherein said solvent is ethanol.

7. The product of claim 1, wherein said binding agent is selected from the group consisting of maltodextrin, dextrose-maltodextrin blends, hydroxypropylmethyl cellulose, carboxymethyl cellulose, polyvinylpyrrolidone, sucrose and mixtures thereof.

8. The product of claim 7, wherein said binding agent is maltodextrin.

9. The product of claim 7, wherein said binding agent is hydroxypropylmethyl cellulose.

10. The product of claim 7, wherein said binding agent is combined with a solvent selected from the group consisting of water, ethanol, isopropanol, methanol and mixtures thereof.

11. The product of claim 10, wherein said solvent is water.

12. The product of claim 7, wherein said carrier is selected from the group consisting of dextrose, citric acid, maltodextrin, dextrose-maltodextrin blends, lactose, inulin, erythritol, sorbitol, sucrose, aspartame, acesulfame salts, sucralose, cyclamate, saccharin, stevioside, alitame and mixtures thereof.

13. The product of claim 12, wherein said carrier is dextrose.

14. The product of claim 12, wherein said carrier is citric acid.

15. The product of claim 12, wherein said carrier is sucrose.

16. The product of claim 12, wherein said carrier is fluidized at a temperature between about 30° C. and about 50° C.

17. The product of claim 16, wherein step (b) comprises heating the premix solution of step (a) to between about 35° C. and about 50° C.

18. The product of claim 1, wherein steps (c) and (d) are performed using a batch fluid bed agglomerator.

19. The product of claim 1, wherein steps (c) and (d) are performed using a continuous fluid bed agglomerator.

20. The product of claim 1, wherein the weight ratio of said N-[N-(3,3-dimethylbutyl)-L-α-aspartyl]-L-phenylalanine 1-methyl ester to said carrier is from about 1:5 to about 1:200.

21. The product of claim 1, wherein said N-[N-(3,3-dimethylbutyl)-L-α-aspartyl]-L-phenylalanine 1-methyl ester is present in an amount from about 0.001 weight percent to about 50 weight percent based upon the total amount of said agglomerate.

22. The product of claim 1, wherein said N-[N-(3,3-dimethylbutyl)-L-α-aspartyl]-L-phenylalanine 1-methyl ester is present-in an amount from about 0.1 weight percent to about 5 weight percent based upon the total amount of said agglomerate.

23. The product of claim 1, wherein said carrier is present in an amount from about 50 weight percent to about 99.9 weight percent based upon the total amount of said agglomerate.

24. The product of claim 1, wherein said carrier is present in an amount from about 75 weight percent to about 99 weight percent based upon the total amount of said agglomerate.

25. The product of claim 1, wherein said binding agent is present in an amount from about 0.1 weight percent to about 15 weight percent based upon the total amount of said agglomerate.

26. The product of claim 1, wherein said binding agent is present in an amount from about 1 weight percent to about 7 weight percent based upon the total amount of said agglomerate.

27. The product of claim 1, wherein said agglomerate is comprised of particles, more than about 80 percent of which are greater in size than 100 mesh and more than about 95 percent of which are greater in size than 140 mesh.

28. The product of claim 27, wherein more than about 70 percent of the particles of said agglomerate are smaller in size than 60 mesh.

29. The product of claim 28, wherein at least 50 percent of the particles of said agglomerate are between about 60 mesh and 100 mesh in size.

30. The product of claim 1, wherein said process of preparing said product further comprises the step of dry blending said agglomerate of step (d) with a blending agent.

31. The product of claim 30, wherein said blending agent comprises a substance selected from the group consisting of aspartame, acesulfame salts, sucralose, saccharin, alitame, cyclamates, stevia derivatives, thaumatin, sucrose, fructose, dextrose, polyol sugar alcohols, dextrin, citric acid, maltodextrin, dextrose-maltodextrin blends, lactose, inulin, erythritol, sorbitol, stevioside, hydroxypropylmethyl cellulose, carboxymethyl cellulose, polyvinylpyrrolidone, N-[N-(3,3-dimethylbutyl)-L-$\alpha$-aspartyl]-L-phenylalanine 1-methyl ester and mixtures thereof.

32. The product of claim 31, wherein said substance is dextrose.

33. The product of claim 31, wherein said substance is maltodextrin.

34. The product of claim 31, wherein said substance is a mixture of dextrose and maltodextrin.

35. The product of claim 31, wherein said substance is lactose.

36. A N-{N-(3,3-dimethylbutyl)-L-$\alpha$-aspartyl}-L-phenylalanine 1-methyl ester agglomerate comprising:
  (i) an effective sweetener amount of N-{N-(3,3-dimethylbutyl)-L-$\alpha$-aspartyl}-L-phenylalanine 1-methyl ester;
  (ii) a binding agent; and
  (iii) a carrier;
wherein said sweetener and binding agent are applied onto the carrier.

37. The agglomerate of claim 36, wherein said binding agent is selected from the group consisting of maltodextrin, dextrose-maltodextrin blends, hydroxypropylmethyl cellulose, carboxymethyl cellulose, polyvinylpyrrolidone, sucrose and mixtures thereof.

38. The agglomerate of claim 37, wherein said binding agent is maltodextrin.

39. The agglomerate of claim 37, wherein said binding agent is hydroxypropylmethyl cellulose.

40. The agglomerate of claim 37, wherein said carrier is selected from the group consisting of dextrose, citric acid, maltodextrin, dextrose-maltodextrin blends, lactose, inulin, erythritol, sorbitol, sucrose, aspartame, acesulfame salts, sucralose, cyclamate, saccharin, stevioside, alitame and mixtures thereof.

41. The agglomerate of claim 40, wherein said carrier is dextrose.

42. The agglomerate of claim 40, wherein said carrier is citric acid.

43. The agglomerate of claim 40, wherein said binding agent and said carrier are the same.

44. The agglomerate of claim 36, wherein the weight ratio of said N-[N-(3,3-dimethylbutyl)-L-$\alpha$-aspartyl]-L-phenylalanine 1-methyl ester to said carrier is from about 1:5 to about 1:200.

45. The agglomerate of claim 36, wherein said N-[N-(3,3-dimethylbutyl)-L-$\alpha$-aspartyl-]-L-phenylalanine 1-methyl ester is present in an amount from about 0.001 weight percent to about 50 weight percent based upon the total amount of said agglomerate.

46. The agglomerate of claim 36, wherein said N-[N-(3,3-dimethylbutyl)-L-$\alpha$-aspartyl]-L-phenylalanine 1-methyl ester is present in an amount from about 0.1 weight percent to about 5 weight percent based upon the total amount of said agglomerate.

47. The agglomerate of claim 36, wherein said carrier is present in an amount from about 50 weight percent to about 99.9 weight percent based upon the total amount of said agglomerate.

48. The agglomerate of claim 36, wherein said carrier age is present in an amount from about 75 weight percent to about 99 weight percent based upon the total amount of said agglomerate.

49. The agglomerate of claim 36, wherein said binding agent is present in an amount from about 0.1 weight percent to about 15 weight percent based upon the total amount of said agglomerate.

50. The agglomerate of claim 36, wherein said binding agent is present in an amount from about 1 weight percent to about 7 weight percent based upon the total amount of said agglomerate.

51. The agglomerate of claim 36, wherein said agglomerate is comprised of particles, more than about 80 percent of which are greater in size than 100 mesh and more than about 95 percent of which are greater in size than 140 mesh.

52. The agglomerate of claim 51, wherein more than about 70 percent of the particles of said agglomerate are smaller in size than 60 mesh.

53. The agglomerate of claim 52, wherein at least 50 percent of the particles of said agglomerate are between about 60 mesh and 100 mesh in size.

54. The agglomerate of claim 36, further comprising a flavor.

55. The agglomerate of claim 36, further comprising a natural or high intensity sweetener.

56. The agglomerate of claim 55, wherein said binding agent is selected from the group consisting of maltodextrin, dextrose-maltodextrin blends, hydroxypropylmethyl cellulose, carboxymethyl cellulose, polyvinylpyrrolidone, sucrose and mixtures thereof.

57. The agglomerate of claim 56, wherein said carrier is selected from the group consisting of dextrose, citric acid, maltodextrin, dextrose-maltodextrin blends, lactose, inulin, erythritol, sorbitol, sucrose, aspartame, acesulfame salts, sucralose, cyclamate, saccharin, stevioside, alitame and mixtures thereof.

58. The agglomerate of claim 57, wherein said natural or high intensity sweetener is selected from the group consisting of aspartame, acesulfame salts, sucralose, saccharin, alitame, cyclamates, stevia derivatives, thaumatin, sucrose, fructose, dextrose, polyol sugar alcohols, and mixtures thereof.

59. A tabletop sweetener comprising a N-{N-(3,3-dimethylbutyl)-L-$\alpha$-aspartyl}-L-phenylalanine 1-methyl ester agglomerate, said agglomerate comprising:
  (i) an effective sweetener amount of N-{N-(3,3-dimethylbutyl)-L-$\alpha$-aspartyl}-L-phenylalanine 1-methyl ester;
  (ii) a binding agent; and
  (iii) a carrier;
wherein said sweetener and binding agent are applied onto the carrier.

60. The tabletop sweetener of claim 59, wherein said binding agent is selected from the group consisting of maltodextrin; dextrose-maltodextrin blends, hydroxypropylmethyl cellulose, carboxymethyl cellulose, polyvinylpyrrolidone, sucrose and mixtures thereof.

61. The tabletop sweetener of claim 60, wherein said binding agent is maltodextrin.

62. The tabletop sweetener of claim 60, wherein said binding agent is hydroxypropylmethyl cellulose.

63. The tabletop sweetener of claim 59, wherein said carrier is selected from the group consisting of dextrose, citric acid, maltodextrin, dextrose-maltodextrin blends, lactose, inulin, erythritol, sorbitol, sucrose, aspartame, acesulfame salts, sucralose cyclamate, saccharin, stevioside, alitame and mixtures thereof.

64. The tabletop sweetener of claim 63, wherein said carrier is dextrose.

65. The tabletop sweetener of claim 63, wherein said carrier is citric acid.

66. The tabletop sweetener of claim 63, wherein said binding agent and said carrier are the same.

67. A tabletop sweetener according to claim 59, wherein said tabletop sweetener comprises:
  (a) N-[N-(3,3-dimethylbutyl)-L-α-aspartyl]-L-phenylalanine 1-methyl ester in an amount from about 0.01 weight percent to about 0.5 weight percent based upon the total amount of said tabletop sweetener;
  (b) maltodextrin in an amount from about 2 weight percent to about 4 weight percent based upon the total amount of said tabletop sweetener; and
  (c) dextrose in an amount from about 96 weight percent to about 98 weight percent based upon the total amount of said tabletop sweetener.

68. A tabletop sweetener according to claim 59, wherein said tabletop sweetener comprises:
  (a) N-[N-(3,3-dimethylbutyl)-L-α-aspartyl]-L-phenylalanine 1-methyl ester in an amount from about 0.01 weight percent to about 0.5 weight percent based upon the total amount of said tabletop sweetener;
  (b) maltodextrin in an amount from about 2 weight percent to about 4 weight percent based upon the total amount of said tabletop sweetener;
  (c) dextrose in an amount from about 92 weight percent to about 97 weight percent based upon the total amount of said tabletop sweetener; and
  (d) aspartame in an amount of from about 1% to about 4% based upon the total amount of said tabletop sweetener.

69. A tabletop sweetener according to claim 59, wherein said tabletop sweetener comprises:
  (a) N-[N-(3,3-dimethylbutyl)-L-α-aspartyl]-L-phenylalanine 1-methyl ester in an amount from about 0.01 weight percent to about 0.5 weight percent based upon the total amount of said tabletop sweetener; and
  (b) sucrose in an amount from about 95 weight percent to about 99.9 weight percent based upon the total amount of said tabletop sweetener.

70. The tabletop sweetener of claim 59, wherein said N-[N-(3,3-dimethylbutyl)-L-α-aspartyl]-L-phenylalanine 1-methyl ester is present in an amount from about $1 \times 10^7$ weight percent to about 50 weight percent based upon the total amount of said tabletop sweetener.

71. The tabletop sweetener of claim 59, wherein said N-[N-(3,3-dimethylbutyl)-L-α-aspartyl]-L-phenylalanine 1-methyl ester is present in an amount from about 0.001 weight percent to about 5 weight percent based upon the total amount of said tabletop sweetener.

72. The tabletop sweetener of claim 59, wherein said carrier is present in an amount from about 0.005 weight percent to about 99.9 weight percent based upon the total amount of said tabletop sweetener.

73. The tabletop sweetener of claim 59, wherein said carrier is present in an amount from about 0.0075 weight percent to about 99 weight percent based upon the total amount of said tabletop sweetener.

74. The tabletop sweetener of claim 59, wherein said binding agent is present in an amount from about 0.00001 weight percent to about 15 weight percent based upon the total amount of said tabletop sweetener.

75. The tabletop sweetener of claim 59, wherein said binding agent is present in an amount from about 0.01 weight percent to about 7 weight percent based upon the total amount of said tabletop sweetener.

76. The tabletop sweetener of claim 59, further comprising a blending agent.

77. The tabletop sweetener of claim 76, wherein said blending agent comprises a substance selected from the group consisting of aspartame, acesulfame salts, sucralose, saccharin, alitame, cyclamates, stevia derivatives, thaumatin, sucrose, fructose, dextrose, polyol sugar alcohols, dextrose, citric acid, dextrin, maltodextrin, dextrose-maltodextrin blends, lactose, inulin, erythritol, sorbitol, stevioside, hydroxypropylmethyl cellulose, carboxymethyl cellulose, polyvinylpyrrolidone, and mixtures thereof.

78. The tabletop sweetener of claim 77, wherein said substance is dextrose.

79. The tabletop sweetener of claim 77, wherein said substance is maltodextrin.

80. The tabletop sweetener of claim 77, wherein said substance is a mixture of dextrose and maltodextrin.

81. The tabletop sweetener of claim 77, wherein said substance is lactose.

82. The tabletop sweetener of claim 76, wherein said blending agent is present in an amount from about 50 weight percent to about 99 weight percent based upon the total amount of said tabletop sweetener.

83. A powdered soft drink mix comprising N-{N-(3,3-dimethylbutyl)-L-α-aspartyl}-L-phenylalanine 1-methyl ester agglomerate, said agglomerate comprising
  (i) an effective sweetener amount of N-{N-(3,3-dimethylbutyl)-L-α-aspartyl}-L-phenylalanine 1-methyl ester;
  (ii) a binding agent; and
  (iii) a carrier;
wherein said sweetener and binding agent are applied onto the carrier.

84. The powdered soft drink mix of claim 83, wherein said binding agent is selected from the group consisting of maltodextrin, dextrose-maltodextrin blends, hydroxypropylmethyl cellulose, carboxymethyl cellulose, polyvinylpyrrolidone, sucrose and mixtures thereof.

85. The powdered soft drink mix of claim 84, wherein said binding agent is maltodextrin.

86. The powdered soft drink mix of claim 84, wherein said binding agent is hydroxypropylmethyl cellulose.

87. The powdered soft drink mix of claim 83, wherein said carrier is selected from the group consisting of dextrose, citric acid, maltodextrin, dextrose-maltodextrin blends, lactose, inulin, erythritol, sorbitol, sucrose, aspartame, acesulfame salts, sucralose, cyclamate, saccharin, stevioside, alitame and mixtures thereof.

88. The powdered soft drink mix of claim 87, wherein said carrier is dextrose.

89. The powdered soft drink mix of claim 87, wherein said carrier is citric acid.

90. The powdered soft drink mix of claim 83, wherein said binding agent and said carrier are the same.

91. The powdered soft drink mix of claim 83, wherein said N-[N-(3,3-dimethylbutyl)-L-α-aspartyl]-L-phenylalanine 1-methyl ester is present in an amount from about 0.00004 weight percent to about 50 weight percent based upon the total weight of said powdered soft drink mix.

92. The powdered soft drink mix of claim 83, wherein said N-[N-(3,3-dimethylbutyl)-L-α-aspartyl]-L-phenylalanine 1-methyl ester is present in an amount from about 0.004 weight percent to about 5 weight percent based upon the total weight of said powdered soft drink mix.

93. The powdered soft drink mix of claim 83, wherein said carrier is present in an amount from about 2 weight percent to about 99.9 weight percent based upon the total amount of said powdered soft drink mix.

94. The powdered soft drink mix of claim 83, wherein said carrier is present in an amount from about 3 weight percent to about 99 weight percent based upon the total amount of said powdered soft drink mix.

95. The powdered soft drink mix of claim 83, wherein said binding agent is present in an amount from about 0.004 weight percent to about 15 weight percent based upon the total amount of said powdered soft drink mix.

96. The powdered soft drink mix of claim 83, wherein said binding agent is present in an amount from about 0.04 weight percent to about 7 weight percent based upon the total amount of said powdered soft drink mix.

97. The powdered soft drink mix of claim 83, further comprising a blending agent.

98. The powdered soft drink mix of claim 97, wherein said blending agent comprise a substance selected from the group consisting of aspartame, acesulfame salts, sucralose, saccharin, alitame, cyclamates, stevia derivatives, thaumatin, sucrose, fructose, dextrose, polyol sugar alcohols, dextrose, citric acid, dextrin, maltodextrin, dextrose-maltodextrin blends, lactose, inulin, erythritol, sorbitol, stevioside, hydroxypropylmethyl cellulose, carboxymethyl cellulose, polyvinylpyrrolidone, and mixtures thereof.

99. The powdered soft drink mix of claim 98, wherein said substance is dextrose.

100. The powdered soft drink mix of claim 98, wherein said substance is maltodextrin.

101. The powdered soft drink mix of claim 98, wherein said substance is a mixture of dextrose and maltodextrin.

102. The powdered soft drink mix of claim 98, wherein said substance is lactose.

103. A sweetener blend comprising a sweetener and a N-{N-(3,3-dimethylbutyl)-L-α-aspartyl}-L-phenylalanine 1-methyl ester agglomerate, said agglomerate comprising:

(i) an effective sweetener amount of N-{N-(3,3-dimethylbutyl)-L-α-aspartyl}-L-phenylalanine 1-methyl ester;

(ii) a binding agent; and (iii) a carrier;

wherein said sweetener and binding agent are applied onto the carrier.

104. The sweetener blend of claim 103, wherein said binding agent is selected from the group consisting of maltodextrin, dextrose-maltodextrin blends, hydroxypropylmethyl cellulose, carboxymethyl cellulose, polyvinylpyrrolidone, sucrose and mixtures thereof.

105. The sweetener blend of claim 104, wherein said binding agent is maltodextrin.

106. The sweetener blend of claim 104, wherein said binding agent is hydroxypropylmethyl cellulose.

107. The sweetener blend of claim 103, wherein said carrier is selected from the group consisting of dextrose, citric acid, maltodextrin, dextrose-maltodextrin blends, lactose, inulin, erythritol, sorbitol, sucrose, aspartame, acesulfame salts, sucralose, cyclamate, saccharin, stevioside, alitame and mixtures thereof.

108. The sweetener blend of claim 107, wherein said carrier is dextrose.

109. The sweetener blend of claim 107, wherein said carrier is citric acid.

110. The sweetener blend of claim 107, wherein said binding agent and said carrier are the same.

111. The sweetener blend of claim 107, wherein said sweetener is selected from the group consisting of aspartame, acesulfame salts, sucralose, saccharin, alitame, cyclamates, stevia derivatives, thaumatin, sucrose, fructose, dextrose, polyol sugar alcohols, and mixtures thereof.

* * * * *